US012173246B2

(12) United States Patent
Ghosh et al.

(10) Patent No.: US 12,173,246 B2
(45) Date of Patent: Dec. 24, 2024

(54) TRACTION FLUID WITH IMPROVED LOW TEMPERATURE CHARACTERISTICS

(71) Applicant: VGP IPCO LLC, Lexington, KY (US)

(72) Inventors: Shibaji Kumar Ghosh, Kolkata (IN); Sulaksha Parab, Goa (IN); Keshav Sopan Badhe, Mumbai (IN); Gefei Wu, Lexington, KY (US); Ning Ren, Naperville, IL (US); Frances E. Lockwood, Georgetown, KY (US)

(73) Assignee: VGP IPCO LLC, Lexington, KY (US)

( * ) Notice: Subject to any disclaimer, the term of this patent is extended or adjusted under 35 U.S.C. 154(b) by 226 days.

(21) Appl. No.: 17/773,438

(22) PCT Filed: Oct. 30, 2019

(86) PCT No.: PCT/US2019/058835
§ 371 (c)(1),
(2) Date: Apr. 29, 2022

(87) PCT Pub. No.: WO2021/086350
PCT Pub. Date: May 6, 2021

(65) Prior Publication Data
US 2022/0403280 A1    Dec. 22, 2022

(51) Int. Cl.
*C10M 127/02* (2006.01)
*C07C 9/22* (2006.01)
(Continued)

(52) U.S. Cl.
CPC .......... *C10M 127/02* (2013.01); *C07C 9/22* (2013.01); *C10M 169/04* (2013.01);
(Continued)

(58) Field of Classification Search
CPC ... C07C 9/22; C07C 2601/14; C07C 2602/42; C10M 127/02; C10M 169/04;
(Continued)

(56) References Cited

U.S. PATENT DOCUMENTS 3,803,037 A * 4/1974 Wygant .................... C10M 3/00
252/75
4,449,415 A * 5/1984 Groenhof ............. C10M 107/50
476/7
(Continued)

FOREIGN PATENT DOCUMENTS

CN    105579563 A    5/2016
CN    108350389 A    7/2018
(Continued)

OTHER PUBLICATIONS

Examination Report issued in Indian Patent Application No. 202217029793, dated Jan. 11, 2023.
(Continued)

*Primary Examiner* — James C Goloboy
(74) *Attorney, Agent, or Firm* — Benesch Friedlander Coplan & Aronoff LLP

(57) ABSTRACT

Traction fluids comprising Formula I, II, III, IV, V, VI, VII or a mixture thereof in combination with a base stock, a viscosity modifier, an anti-foaming agent, and an additive package.

18 Claims, 1 Drawing Sheet

(51) Int. Cl.
  *C10M 169/04* (2006.01)
  *C10N 20/02* (2006.01)
  *C10N 30/02* (2006.01)
  *C10N 30/18* (2006.01)
  *C10N 40/04* (2006.01)

(52) U.S. Cl.
  CPC ...... *C07C 2601/14* (2017.05); *C07C 2602/42* (2017.05); *C10M 2203/003* (2013.01); *C10M 2203/04* (2013.01); *C10N 2020/02* (2013.01); *C10N 2030/02* (2013.01); *C10N 2030/18* (2013.01); *C10N 2040/04* (2013.01); *C10N 2040/046* (2020.05)

(58) Field of Classification Search
  CPC ............ C10N 2020/02; C10N 2030/02; C10N 2030/18; C10N 2040/04; C10N 2040/046
  See application file for complete search history.

(56) References Cited

U.S. PATENT DOCUMENTS

| | | | |
|---|---|---|---|
| 6,623,399 | B2 | 9/2003 | Fey et al. |
| 6,797,680 | B2 | 9/2004 | Chapaton et al. |
| 6,828,283 | B2 | 12/2004 | Chapaton et al. |
| 7,402,715 | B2 * | 7/2008 | Yoshida ............... C10M 111/02 252/73 |
| 2004/0152607 | A1 | 8/2004 | Chapaton et al. |
| 2004/0152931 | A1 | 8/2004 | Chapaton et al. |
| 2007/0057226 | A1 * | 3/2007 | Forbus ................. C10M 169/04 252/73 |

FOREIGN PATENT DOCUMENTS

| | | |
|---|---|---|
| EP | 0748863 A2 | 12/1996 |
| EP | 0968987 A1 | 5/2000 |
| JP | S54-040351 A | 3/1979 |
| JP | S54-108876 | 7/1979 |
| JP | H03-095295 A | 4/1991 |
| JP | H051292 A | 1/1993 |
| JP | H11-349968 A | 12/1999 |
| JP | 2000-017280 A | 1/2000 |
| JP | 2001-247492 A | 9/2001 |
| JP | 2001-294881 A | 10/2001 |
| JP | 2010059274 A | 3/2010 |
| JP | 2019-131637 A | 8/2019 |
| JP | 2019156978 A | 9/2019 |
| WO | 2019/189502 A1 | 10/2019 |
| WO | 2020186139 A1 | 9/2020 |

OTHER PUBLICATIONS

International Search Report and Written Opinion dated Jan. 27, 2020 for PCT Application No. PCT/US19/58835, 12 pages.
Sabatier, P. et al., "Preparation of Dicyclohexylbutanes," Chemical Abstracts Service, Compt. rend. (1913), 156, 1430-4, 1 page.
Extended European Search Report dated Apr. 5, 2023 for European Application No. 19951079.3, 8 pages.
Communication pursuant to Article 94(3) EPC issued in European Patent Application No. 19951079.3, dated Apr. 10, 2024.
Notice of Allowance issued in Canadian Patent Application No. 3,156,420 dated Apr. 15, 2024.

* cited by examiner

| | Blend-1 (Reference) | Blend-2 | Blend-3 | Blend-4 | Blend-5 | Blend-6 | Blend-7 | Formula-II | Formula-III | Formula-IV & V | Formula VI | Formula VII | Blend-8 | Blend-9 |
|---|---|---|---|---|---|---|---|---|---|---|---|---|---|---|
| DI package | 5.7 | 5.7 | 5.7 | 5.7 | 5.7 | 5.7 | 5.7 | - | - | - | - | - | 5.7 | 5.7 |
| HAD | 92.2 | 82.2 | 45.4 | 82.2 | 45.4 | 82.2 | 45.8 | - | - | - | - | - | 71.8 | 46.2 |
| Formula II | - | 10 | 45.4 | - | - | - | - | 100 | - | - | - | - | - | - |
| Formula III | - | - | - | 10 | 45.4 | - | - | - | 100 | - | - | - | - | - |
| Formula IV and V | - | - | - | - | - | 10 | 45.8 | - | - | 100 | - | - | - | - |
| Formula VI | - | - | - | - | - | - | - | - | - | - | 100 | - | 20 | - |
| Formula VII | - | - | - | - | - | - | - | - | - | - | - | 100 | - | 46 |
| Viscosity modifier | 2 | 2 | 3.4 | 2 | 3.4 | 2 | 2.6 | - | - | - | - | - | 2.4 | 2 |
| Antifoaming agent | 0.1 | 0.1 | 0.1 | 0.1 | 0.1 | 0.1 | 0.1 | - | - | - | - | - | 0.1 | 0.1 |
| Kinematic viscosity@100C (cSt) | 4.88 | 4.62 | 4.66 | 4.76 | 4.94 | 4.85 | 4.92 | 2.29 | 2.6 | 2.94 | 2.58 | 3.43 | 4.8 | 4.93 |
| Kinematic viscosity@40C (cSt) | 26.73 | 24.62 | 22.52 | 22.97 | 22.74 | 25.66 | 23.6 | 10.3 | 10.24 | 12.27 | 10.55 | 19.31 | 24.19 | 27.47 |
| Brookfield viscosity (cP) -30C | 26,200 | 21,500 | 13,000 | 20,350 | 7,860 | 20,500 | 7840 | 5700 | 1730 | 1740 | 2470 | 8460 | 16,950 | 15,600 |
| Coefficient of traction | 0.0942 | 0.0933 | 0.0886 | 0.0940 | 0.0907 | 0.0941 | 0.0911 | 0.0867 | 0.0895 | 0.0906 | 0.0893 | 0.897 | 0.0928 | 0.0923 |
| Traction loss (%) | - | 0.96 | 5.94 | 0.21 | 3.72 | 0.11 | 2.97 | 7.96 | 4.99 | 3.82 | 5.2 | 4.77 | 1.48 | 2.01 |
| Improvement in Brookfield viscosity (cP) -30C (%) | - | 17.94 | 50.38 | 22.33 | 70 | 21.76 | 70.08 | 78.24 | 93.4 | 93.36 | 90.57 | 67.7 | 35.3 | 40.45 |

FIG: 1A

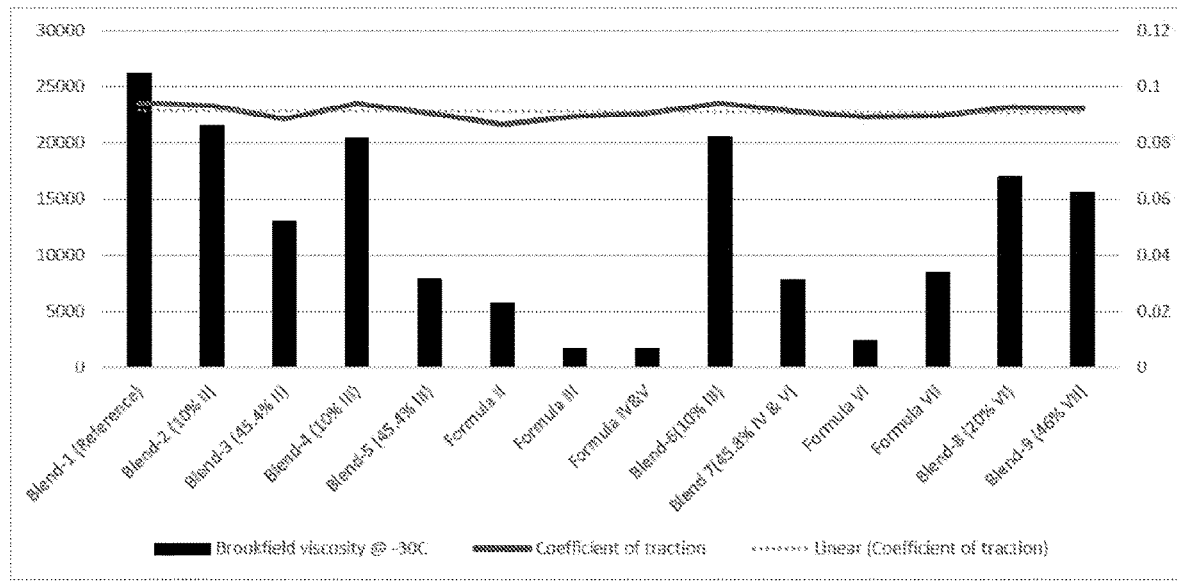

FIG: 1B

TRACTION FLUID WITH IMPROVED LOW TEMPERATURE CHARACTERISTICS

CROSS-REFERENCE TO RELATED APPLICATIONS

The present application is a U.S. National Stage Entry of PCT International Patent Application No. PCT/US2019/058835 entitled "TRACTION FLUID WITH IMPROVED LOW TEMPERATURE CHARACTERISTICS," filed on Oct. 30, 2019, the disclosure of which is hereby incorporated by reference in its entirety.

FIELD OF INVENTION

The present disclosure generally relates to a traction fluid blend with improved viscosity at low temperatures.

BACKGROUND

With traction drive technology, power can be transmitted through a thin fluid film placed in between a rolling contact interface. This fluid, popularly called traction fluid, transfers force while also keeping the bodies separated to minimize surface wear. Traction fluids rely on its high shear strength to provide torque transmission in devices like continuous variable transmission (CVT) or infinite variable transmission (IVT). Such transmission allows seamless integration with internal combustion engine for optimal engine performance and maximum fuel efficiency. In the year 1999, toroidal continuous variable transmission (T-CVT) cars were introduced in the market and the traction fluid used for the T-CVT required high level of performance in terms of high traction coefficient and low temperature fluidity of the molecule.

SUMMARY

Traction fluids with a base oil of the general structure:

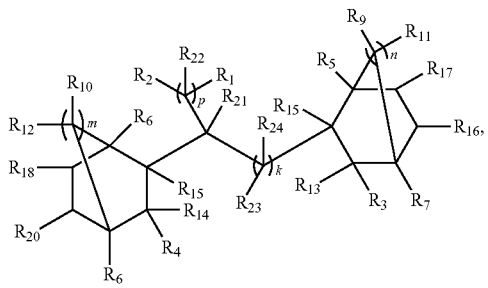

(Formula I)

where $R_1$-$R_{24}$ are each independently a H, methyl, ethyl, propyl, iso-propyl, butyl, iso-butyl or tertbutyl group; k, m, n, and p are each independently $C_0$-$C_3$; and the fluid additionally containing additive packages, anti-foaming agents and viscosity modifiers are provided.

BRIEF DESCRIPTION OF THE DRAWINGS

In the accompanying figures, chemical formulas, chemical structures, and experimental data are given that, together with the detailed description provided below, describe example embodiments.

FIG. 1A is a table summarizing the properties of traction fluid formulations of the invention. FIG. 1B is representative graph of the FIG. 1A table data.

DETAILED DESCRIPTION

Base fluid includes a base oil of the general structure:

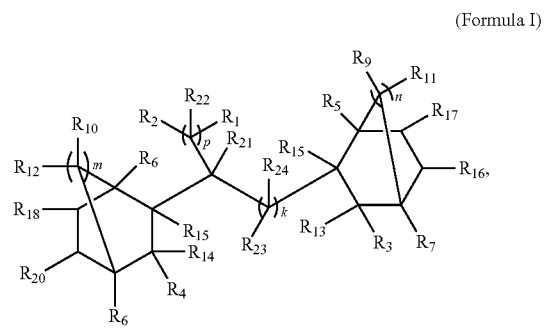

(Formula I)

where $R_1$-$R_{24}$ are each independently a H, methyl, ethyl, propyl, iso-propyl, butyl, iso-butyl or tertbutyl group; k, m, n, and p are each independently $C_0$-$C_3$;

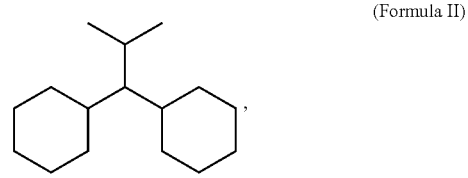

(Formula II)

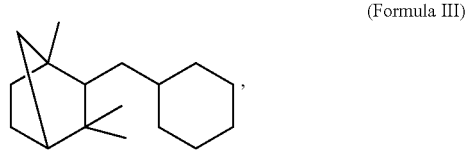

(Formula III)

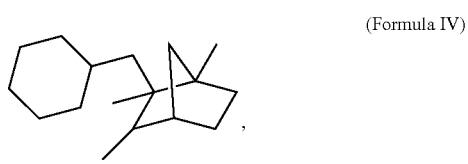

(Formula IV)

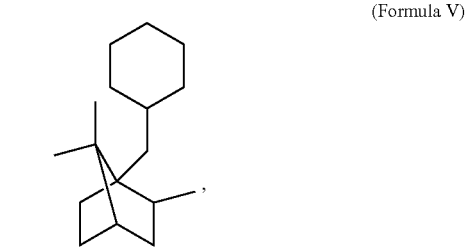

(Formula V)

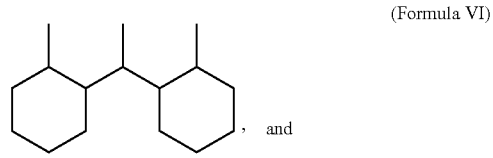

(Formula VI)

, and

-continued (Formula VII)

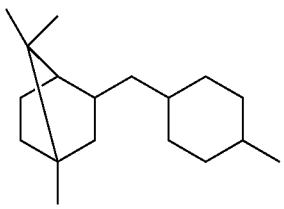

A combination of Formula I, II, III, IV, V, VI, VII serves as a foundation of a traction fluid to which additional additives and traction fluids may be added to form fully-formulated traction fluid. The traction fluid may comprise a blend of Formulas I, II, III, IV, V, VI and VII in any combination. These additives include antioxidant agents, antiwear agents, extreme pressure agents, detergents, dispersants, antifoamers, anti-rust agents, friction modifiers, or viscosity modifiers. The additives may be provided as an additive package.

In some cases, the traction fluids comprising Formula I, II, III, IV, V, VI, VII may be characterized by a Brookfield viscosity (cP) @−30° C. of between about 1730 and 21500, or a traction coefficient of between about 0.0867 and about 0.0933 or a kinematic viscosity (cSt) @40° C. of between about 10.24 and 24.62.

The traction fluids comprising Formula I, II, III, IV, V, VI, VII may be characterized by Formula I, II, III, IV, V, VI, VII or a mixture thereof in an amount between about 0.1 wt % and about 50 wt and a base stock in an amount between about 30 wt % and about 9938 wt %: a viscosity modifier in an amount between about 0.01 wt % and about 10 wt %; an anti-foaming agent in an amount between about 0.1 wt % and about 0.5 wt %; and an additive package in an amount between about 0.01 wt % and about 10 wt %.

Base Oil

Formula I, II, III, IV, V, VI, VII or a combination of Formula I, II, III, IV, V, VI and VII may serve as a supplement to a base oil or base stock for a final fully formulated traction fluid. A traction fluid may also comprise a combination of Formula I, II, III IV, V, VI and VII with other base stocks in varying ratios.

The base stocks may be selected from the group consisting of mineral oils (Group I, II or III oils), polyalphaolefins (Group IV oils), polymerized and interpolymerized olefins, alkyl naphthalenes, alkylene oxide polymers, silicone oils, phosphate esters and carboxylic acid esters (Group V oils). The base stocks may be selected from a group comprising HAD (hydrogenated alpha dimethyl styrene), isoHAD, blends thereof.

Definitions for the base stocks in this invention are the same as those found in the American Petroleum Institute (API) publication "Engine Oil Licensing and Certification System", Industry Services Department, Fourteenth Edition, December 1996. Addendum 1, December 1998. Said publication categorizes base stocks as follows: a) Group I base stocks contain less than 90 percent saturates and/or greater than 0.03 percent sulfur and have a viscosity index greater than or equal to 80 and less than 120 using the test methods specified in the following table b) Group II base stocks contain greater than or equal to 90 percent saturates and less than or equal to 0.03 percent sulfur and have a viscosity index greater than or equal to 80 and less than 120 using the test methods specified in the following table c) Group III base stocks contain greater than or equal to 90 percent saturates and less than or equal to 0.03 percent sulfur and have a viscosity index greater than or equal to 120.

Base stocks for traction fluids are saturated ring compounds. These alicyclic compounds may contain monocyclic, polycyclic or bridge cyclic hydrocarbons, or a combination of the aforementioned.

Viscosity Modifiers

The traction fluids may contain a viscosity modifier or a combination of viscosity modifiers. The viscosity improvers used in the lubricant industry can be used in the instant invention for the oil medium, which include olefin copolymers (OCP), polymethacrylates (PMA), hydrogenated styrene-diene (STD), and styrene-polyester (STPE) polymers. Olefin copolymers are rubber-like materials prepared from ethylene and propylene mixtures through vanadium-based Ziegler-Natta catalysis. Styrene-diene polymers are produced by anionic polymerization of styrene and butadiene or isoprene. Polymethacrylates are produced by free radical polymerization of alkyl methacrylates, Styrene-polyester polymers are prepared by first co-polymerizing styrene and maleic anhydride and then esterifying the intermediate using a mixture of alcohols.

Other compounds which can be used in the instant invention in the oil medium include: acrylic polymers such as polyacrylic acid and sodium polyacrylate, high-molecular-weight polymers of ethylene oxide such as Polyox WSR from Union Carbide, cellulose compounds such as carboxymethylcellulose, polyvinyl alcohol (PVA), polyvinyl pyrrolidone (PVP), xanthan gums and guar Mims, polysaccharides, alkanolamides, amine salts of polyamide, hydrophobically modified ethylene oxide urethane, silicates, and fillers such as mica, silicas, cellulose, wood flour, clays (including organoclays) and clays, and resin polymers such as polyvinyl butyral resins, polyurethane resins, acrylic resins and epoxy resins.

The viscosity modifiers may include a combination of more than one viscosity modifier. The viscosity modifiers may be added in an amount between about 0.01 wt % and about 10 wt %. The additive amount may also be described by ally single digit found in the range between about 0.01 (w/w) % and less than about 10 (wily) such as 2.0 or 3.4 wt %.

Antifoamers

In addition to any defoamer or antifoamer that may be present in the additive package, at least one additional antifoamer may be added to the traction fluid. Preferably, at least two antifoamers are added to the traction fluid. More than two antifoamers may also be added to the traction fluid. The traction fluid may include an anti-foaming agent that is an organic acid ester, a siloxane, a silicone based fluid or a combination of any of these compounds. One antifoamer, may include a mixture of compounds such as an organic acid ester and siloxane, such as, for example, the commercially available Nalco 2301. One antifoamer may be silicone based, such as for example the commercially available Chemaloy F-655.

The traction fluid may include the anti-foaming agent in an amount greater than about 0.01 (w/w) % and less than about 0.5 (w/w) %. The anti-foaming agent maybe present in an amount of about 0.1 (w/w) %. The anti-foaming agent may be described by any single digit found in the range between about 0.01 (w w) % and less than about 0.5 (w/w) %, such as 0.1 wt %. The anti-foaming agent may be a mixture of organic acid ester and siloxane or a silicone based fluid. The traction fluid may contain one, two or more than two anti-foaming agents. The antifoaming agent may comprise any appropriate defoamer.

Additive Package

The traction fluids may also include at least one performance additive package. The performance additive package is generally a fully formulated composition, including antioxidant agents, antiwear agents, extreme pressure agents, detergents, dispersants, antifoamer, anti-rust agents, friction modifiers, corrosion inhibitors, and pour point depressants. The performance additive package may be commercially available, such as DI package, and used as directed by manufacturer. Additives such as a colorant or dye may also be added to the traction fluid.

Dispersants commonly used in the automotive industry contain a lipophilic hydrocarbon group and a polar functional hydrophilic group. The polar functional group can be of the class of carboxylate, ester, amine, amide, imine, imide, hydroxyl, ether, epoxide, phosphorus, ester carboxyl, anhydride, or nitrile. The lipophilic group can be oligomeric or polymeric in nature, usually from 70 to 200 carbon atoms to ensure good oil solubility. Hydrocarbon polymers treated with various reagents to introduce polar functions include products prepared by treating polyolefins such as polyisobutene first with maleic anhydride, or phosphorus sulfide or chloride, or by thermal treatment, and then with reagents such as polyamine, amine, ethylene oxide, etc. A surfactant or a mixture of surfactants with low HLB value (typically less than or equal to 8), preferably nonionic, or a mixture of nonionics and ionics, may be used as a dispersant.

Other chemical compounds, preferably polymers, not for the purpose of dispersing, but to achieve thickening or other desired fluid characteristics. These can be added but reduce the amount of particulate that can be used without excessive thickening.

Chemical compounds such as seal swell agents or plasticizers can also be used in the instant invention and may be selected from the group including phthalate, adipate, sebacate esters, and more particularly: glyceryl tri(acetoxystearate), epoxidized soybean oil, epoxidized linseed oil, N, n-butyl benzene sulfonamide, aliphatic polyurethane, epoxidized soy oil, polyester glutarate, polyester glutarate, triethylene glycol caprate/caprylate, long chain alkyl ether, dialkyl diester glutarate, monomeric, polymer, and epoxy plasticizers, polyester based on adipic acid, hydrogenated dimer acid, distilled dimer acid, polymerized fatty acid trimer, ethyl ester of hydrolyzed collagen, isostearic acid and sorbian oleate and cocoyl hydrolyzed keratin, PPG-12/PEG-65 lanolin oil, dialkyl adipate, alkylaryl phosphate, alkyl diaryl phosphate, modified triaryl phosphate, triaryl phosphate, butyl benzyl phthalate, octyl benzyl phthalate. alkyl benzyl phthalate, dibutoxy ethoxy ethyl adipate, 2-ethylhexyldiphenyl phosphate, dibutoxy ethoxy ethyl formyl, diisopropyl adipate, diisopropyl sebacate, isodecyl oleate, neopentyl glycol dicaprate, neopenty glycol diotanoate, isohexyl neopentanoate, ethoxylated lanolins, polyoxyethylene cholesterol, propoxylated (2 moles) lanolin alcohols, propoxylated lanoline alcohols, acetylated polyoxyethylene derivatives of lanoline, and dimethylpolysiloxane. Other plasticizers which may be substituted for and/or used with the above plasticizers including glycerine, polyethylene glycol, dibutyl phthalate, and 2,2,4-trimethyl-L3-pentanediol monoisobutyrate, and diisononyl phthalate all of which are soluble in a solvent carrier. Other seal swelling agents such as LUBRIZOL 730 can also be used.

Pour point depressants, either of polymethyl methacrylate or ethylene propylene olefin co-polymer type are useful to decrease the low temperature Brookfield viscosity of the fluid.

The traction fluid may comprise, in addition to the base stock and additive package, other additives. Any additive that may improve the properties or functioning of the traction fluid may be added. The traction fluid may also comprise additives m an amount greater than about 0.01 (w/w) % and less than about 10 (w/w) %. The amount of any one additive may be in an amount between 0.01 (w/w) % and less than about 10 (w/w) %. If more than one additive is added to the formulation, the total amount of additives present may be in an amount from 0.01 (w/w) % and less than about 10 (w/w) %. Alternatively, the amount 0.01 (w/w) % and less than about 10 (w/w) % may refer to the each additive present in the traction fluid.

The additive may comprise, may consist essentially of or consist of a single ingredient, such as one de-foaming agent. Alternatively, the additive may comprise, may consist essentially of or consist of a commercially available additive package. The additive may comprise, may consist essentially of or consist of a viscosity modifier. The additive may comprise, may consist essentially of or consist of a combination of a defoamer, viscosity modifier and a transmission additive package.

EXAMPLES

Certain embodiments are described below in the form of examples. While the embodiments are described in considerable detail, it is not the intention to restrict or in any way limit the scope of the appended claims to such detail, or to any particular embodiment.

Tractions fluid described herein may comprise, as part of the final formulation of a traction fluid, a compound with the general structure:

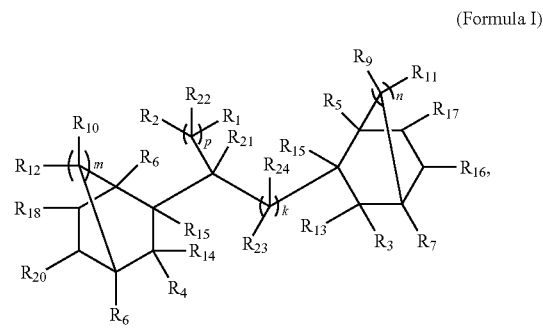

(Formula I)

where $R_1$-$R_{24}$ are each independently a H, methyl, ethyl, propyl, iso-propyl, butyl, iso-butyl or tertbutyl group; k, m, n, and p are each independently $C_0$-$C_3$.

Example 1: Synthesis

A general structure of Formula II and Formula VI can be summarized as follows:

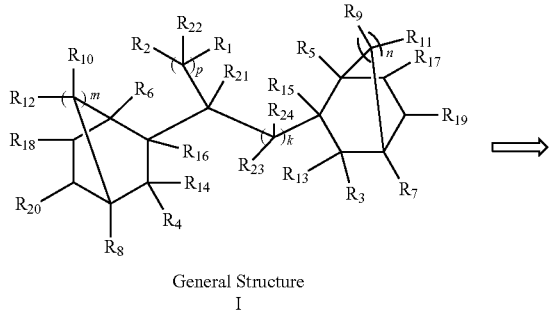

General Structure I

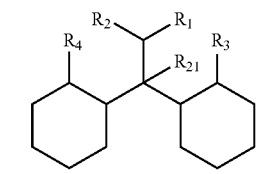

II  $R_1$ & $R_2$ = Me, $R_3$ to $R_{24}$ = H, k, m & n = 0, p = 1
VI  $R_3$, $R_4$ & $R_{21}$ = Me, $R_1$, $R_2$, $R_5$ to $R_{20}$, $R_{22}$ to $R_{24}$ = H, k, m, n & p = 0

As specific examples, Formula II & VI may be synthesized as follows:

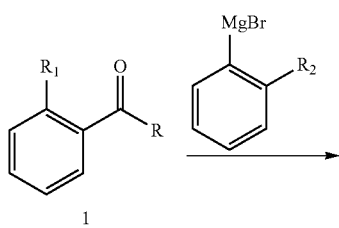

1

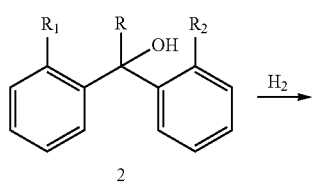

2

II R = iPr, $R_1$ & $R_2$ = H
VI R, $R_1$, $R_2$ = Me

A general structure of Formula III and VII can be summarized as follows:

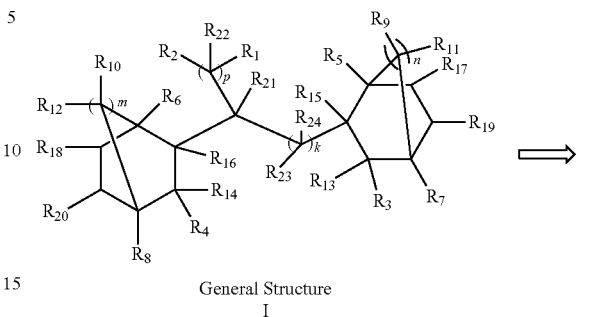

General Structure I

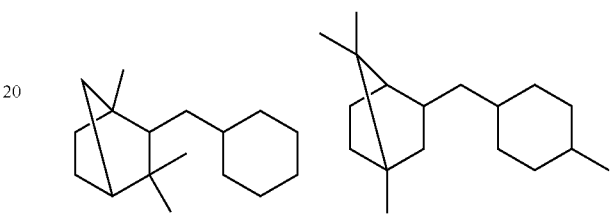

III   $R_1$ to $R_3$, $R_5$, $R_7$ to $R_{13}$ & $R_{15}$ to $R_{24}$ = H, $R_4$, $R_6$ & $R_{14}$ = Me, k = 0, m = 1, n = 0, p = 0
VII $R_1$ to $R_7$, $R_9$, $R_{11}$, $R_{13}$ to $R_{18}$ & $R_{20}$ to $R_{24}$ = H, $R_8$, $R_{10}$, $R_{12}$ & $R_{15}$ = Me, m = 1, k, n & p = 0

As specific examples, Formula III and Formula VII may be synthesized as follows:

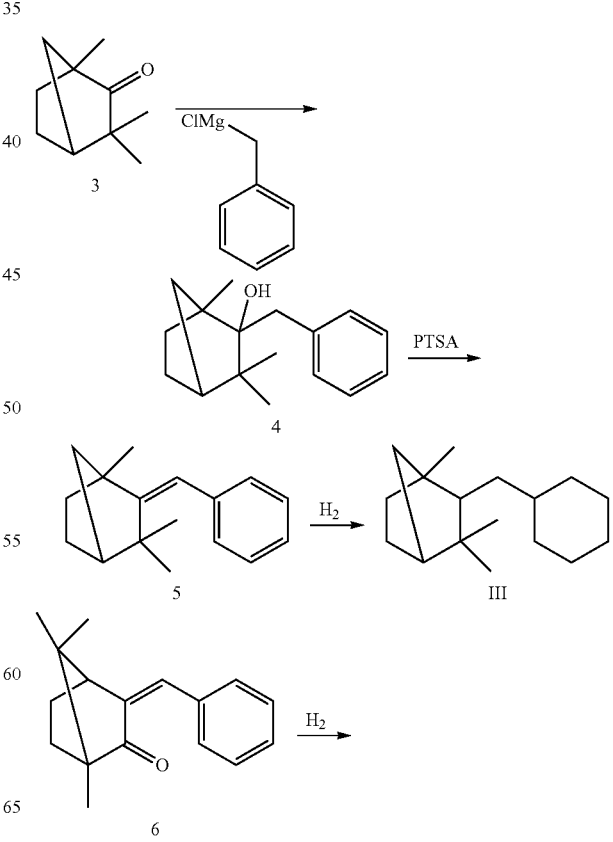

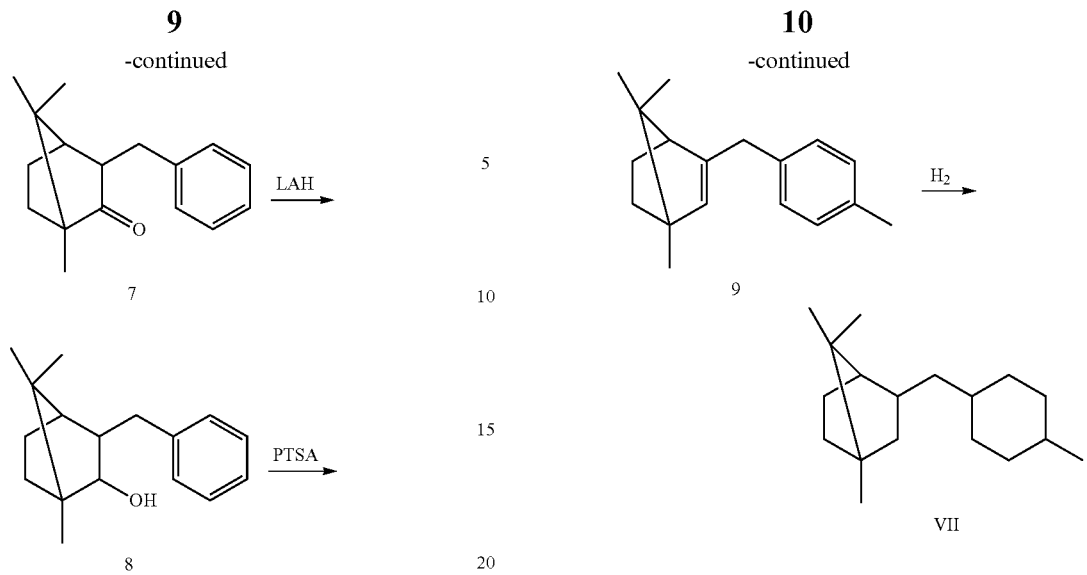
Synthesis of a blend of Formulas III, IV and V can be summarized as follows:
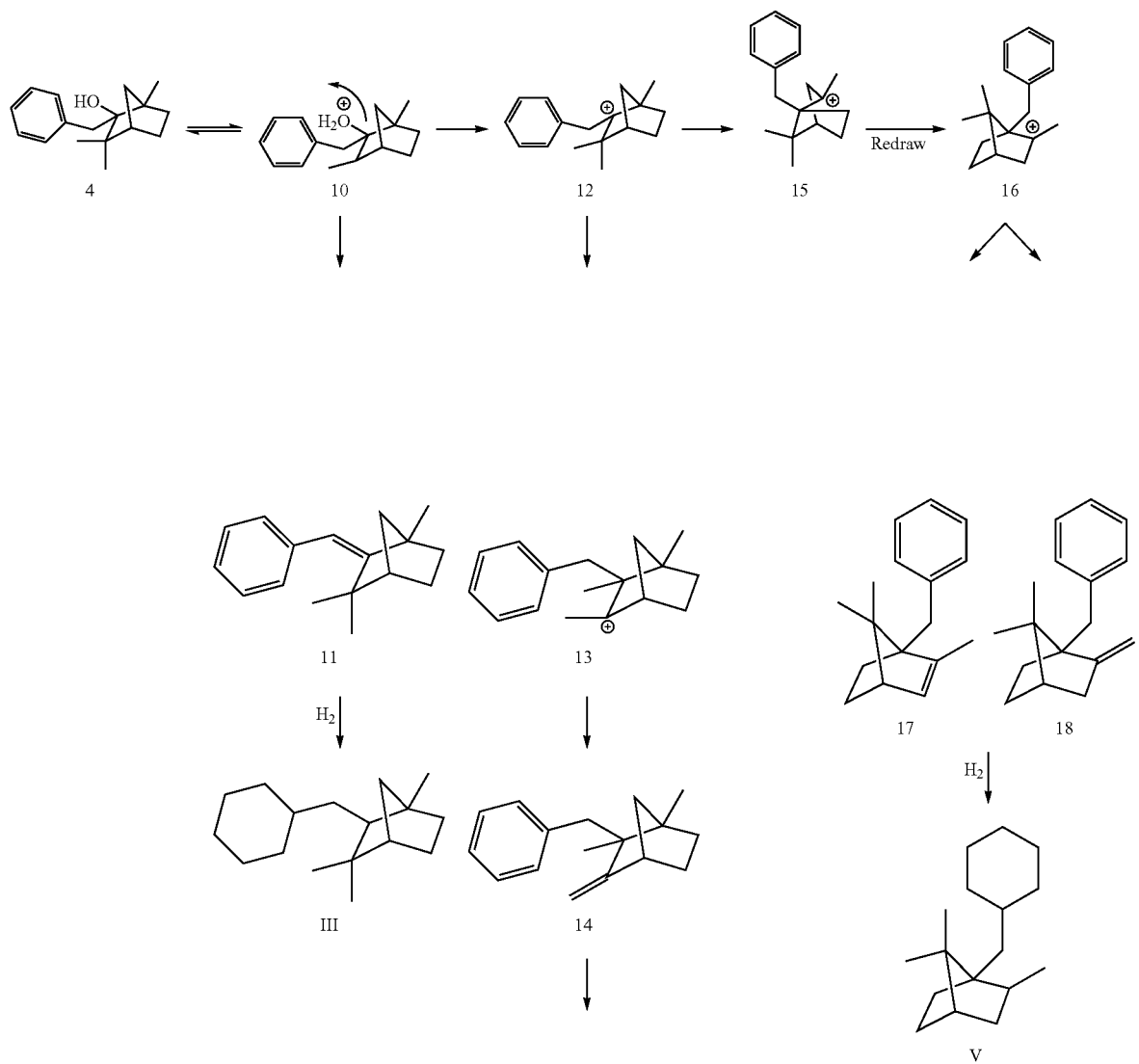

-continued

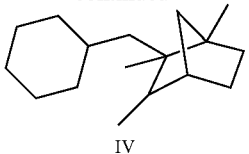

IV

In this case the blend comprises 60% of a mixture of Formula IV and V+40% Formula III.

Example 2: Analysis of Traction Fluid Formulations

Referring, now to FIG. 1A, experimental data with pure and formulated traction fluids is shown. The data is represented graphically in FIG. 1B. As a pure material, Formula II and VI shows 78.24% and 90.57% improvement in Brookfield viscosity (BF) at −30° C. with 7.96% and 5.2% traction loss respectively as compared to Blend-1 (reference fluid). Blends, such as Blend 2 in FIG. 1A, comprising 10% by wt Formula II demonstrated 17.94% BF viscosity improvement while keeping the traction coefficient almost the same. Blend 3, comprising 45.4% of Formula II had a 50.38% BF viscosity improvement with 5.94% traction loss. Blend 8, comprising 20% of Formula VI had a 35.3% BF viscosity improvement with only 1.48% traction loss. (See FIG. 1A).

Referring now to formulations comprising Formula III and VII, as a pure material Formula III and VII shows 93.4% and 67.7% improvement in Brookfield viscosity (BF) at −30° C. with 4.99% and 4.77% traction loss compared to Blend-1 (reference fluid). Blends comprising Formula III, such as Blend 4, with 10 wt % Formula III had a 22.33% BF viscosity improvement while keeping the traction coefficient almost same. Blend 5, with 45.4% of Formula III shows 70% BF viscosity improvement with 3.72% traction loss. Blend 9, with 46% of Formula VII shows 40.45% BF viscosity improvement with only 2.0% traction loss (See FIG. 1A).

Referring now to a blend of Formulas III, IV and V as exemplified by Blends 6 and 7 of FIG. 1A and FIG. 1B, formulations containing this blend perform similarly to Formula III alone.

This remarkable low temperature improvement without compromising traction coefficient has lot of potential as INIT fluid application in extremely demanding conditions.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11. The term wt is meant to describe a comparison of the weight of one compound to the weight of the whole composition expressed as a percent. It can also be described as wt. %, or (w/w) %. The term defoamer is equivalent to antifoamer, anti-foamer, or de-foamer and includes any substance that reduces or hinders the formation of foam in a traction fluid. The terms base oil and base stock are interchangeable and refer to a fluid that is present in an amount greater than about 70% and forms the basis of a traction fluid.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A traction fluid comprising at least one compound of:

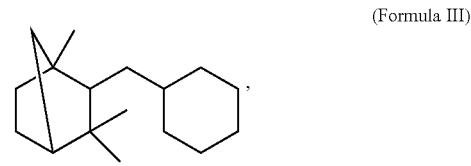

(Formula III)

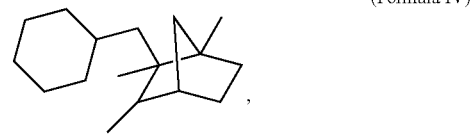

(Formula IV)

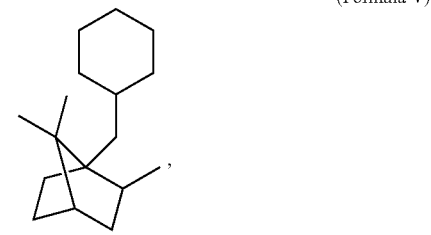

(Formula V)

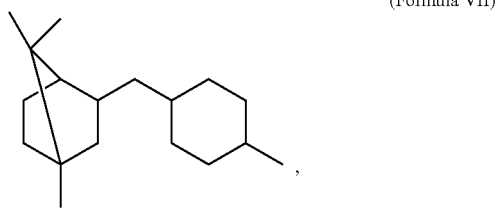

(Formula VII)

or a combination thereof.

2. The traction fluid of claim 1, wherein Formula III, IV, V, VII or a mixture thereof are present in amount between about 0.1 wt % and about 50 wt % of a final formulation of a traction fluid.

3. The traction fluid of claim 1 further comprising a traction fluid base stock in an amount between about 30 wt % and about 99.78 wt % of the final formulation.

4. The traction fluid of claim 1 further comprising a traction fluid base stock in an amount between about 45.4 wt % and about 92.2 wt % of the final formulation.

5. The traction fluid of claim 1 further comprising an anti-foaming agent.

6. The traction fluid of claim 1 further comprising an anti-foaming agent in an amount between about 0.01 wt % and about 0.5 wt % of the final formulation.

7. The traction fluid of claim 1 further comprising an anti-foaming agent in an amount of about 0.1 wt %.

8. The traction fluid of claim 1 further comprising a viscosity modifier.

9. The traction fluid of claim 1 further comprising a viscosity modifier in an amount between about 0.01 wt % and about 10 wt %.

10. The traction fluid of claim 1 further comprising a viscosity modifier in an amount between about 2 wt % and about 3.4 wt % of the final formulation.

11. The traction fluid of claim 1, further comprising at least one additive selected from the group consisting of: antioxidant agents, antiwear agents, extreme pressure agents, detergents, dispersants, antifoamer, anti-rust agents, friction modifiers, corrosion inhibitors, pour point depressants, and a combination thereof, wherein the combination thereof constitutes an additive package.

12. The traction fluid of claim 11, wherein the additive package is present in an amount between about 0.01 wt % and about 10 wt % of the final formulation.

13. The traction fluid of claim 11, wherein the additive package in an amount of about 5.7 wt %.

14. The traction fluid of claim 1, further comprising a base stock, viscosity modifier, an anti-foaming agent and an additive package.

15. A traction fluid comprising:
    a compound of Formula III, IV, V, VII or a mixture thereof of claim 2 in an amount between about 0.1 wt % and about 50 wt %;
    base stock in an amount between about 30 wt % and about 99.78 wt %;
    a viscosity modifier in an amount between about 0.01 wt % and about 10 wt %;
    an anti-foaming agent in an amount between about 0.1 wt % and about 0.5 wt %; and
    additive package in an amount between about 0.01 wt % and about 10 wt %.

16. The traction fluid of claim 1 having a Brookfield viscosity (cP) @-30° C. of between about 1730 and 21500.

17. The traction fluid of claim 1 having a traction coefficient of between about 0.0867 and about 0.0933.

18. The traction fluid of claim 1 having a kinematic viscosity (cSt) @40° C. of between about 10.24 and 24.62.

* * * * *